United States Patent [19]

Bakke et al.

[11] 4,418,230

[45] Nov. 29, 1983

[54] METHOD FOR GASEOUS PHASE NITRATION OF AROMATICS

[75] Inventors: Jan Bakke, Hommelvik; Jermünd Liaskar, Volda, both of Norway

[73] Assignee: Aktiebolaget Bofors, Bofors, Sweden

[21] Appl. No.: 338,809

[22] Filed: Jan. 11, 1982

Related U.S. Application Data

[63] Continuation of Ser. No. 917,449, Jun. 21, 1978, abandoned.

[51] Int. Cl.$^3$ ............................................. C07C 79/10
[52] U.S. Cl. ................................... 568/940; 568/939
[58] Field of Search .................... 568/937, 939, 940

[56] References Cited

U.S. PATENT DOCUMENTS 3,928,476 12/1975 Shimada et al. .................... 568/937
4,107,220 8/1978 Owsley et al. ...................... 568/937
4,112,006 9/1978 Schubert et al. .................... 568/940

FOREIGN PATENT DOCUMENTS 2510095 9/1975 Fed. Rep. of Germany .
1484589 9/1977 United Kingdom .

OTHER PUBLICATIONS

The Condensed Chemical Dictionary, Reinhold Pub. Corp., N.Y., 1956, pp. 286, 739 and 1186.

*Primary Examiner*—Leland A. Sebastian
*Attorney, Agent, or Firm*—Pollock, Vande Sande & Priddy

[57] ABSTRACT

Nitration of aromatics wherein gasified aromatic compounds and nitric acid are contacted with a silicon-aluminum catalyst.

13 Claims, No Drawings

METHOD FOR GASEOUS PHASE NITRATION OF AROMATICS

This is a continuation of application Ser. No. 917,449, filed June 21, 1978, now abandoned.

The present invention relates to a method of producing nitrated aromatic compounds, which method involves a gaseous phase nitration. The nitrated aromatic compounds, the nitro-aromatics, are products of importance to the chemical industry, both as such and as intermediates for further processing.

As a rule, nitrations of aromatics have previously been carried out in a liquid phase with nitric acid and with sulphuric acid as a catalyst. Such processes involve that the sulphuric acid, which is a highly corrosive liquid, must be regenerated which, in turn, involves cost increases as regards both work and apparatus. At the nitration of substituted benzenes, there is also the problem of the relation between the different isomers obtained. Thus, at the nitration of toluene, normally approx. 60% ortho, 3% meta, and 37% para-isomers are obtained. As the orthonitrotoluene is the one which has the least value, there is, of course, an interest in methods with more favourable isomer relations.

Processes with solid catalysts or processes which give a greater yield of the isomer desired have previously been described. In these processes, however, either catalysts which have a short life and which are difficult to regenerate, or else catalysts which are highly corrosive, have been used.

Through the present invention, it has now proved to be possible to cope with the above-mentioned drawbacks. The characteristic features of the invention will be noted from the accompanying claims.

According to the invention, heterogeneous catalysts are used, and then particularly acid catalysts of the siliconaluminium type. The aromatic compound in question is conveyed together with nitric acid in a gaseous phase over catalysts, and the reaction seems to take place at the boundary between the gaseous and the solid phase. The catalysts used here are mechanically stable, and easy to regenerate when the activity decreases. They have also been used for a long time in other connections, e.g. in petrochemical processes.

Tests which have been carried out have shown that the activity is high for nitration, and that comparatively small continuous reactors can given large quantities of nitro-aromatics.

The tests also show that a greater reaction is obtained when the catalyst is finely distributed, and this is in all probability due to the fact that the diffusion of the reaction components in the catalyst particles is a speed-limiting factor.

Finally, the tests have shown that an economically more favourable isomer relation is obtained with the present invention than with conventional liquid phase nitration with sulphuric acid as a catalyst.

The invention will now be described in more detail, with reference to the tests accounted for in the following.

Aromatic and 65% nitric acid were gasified individually and conveyed together with nitrogen into a reactor. This, which consists of a glass tube which can be heated, with an inner diameter of 10 mm, was provided with a thermometer pocket and a glass sinter. The catalyst used, which amounted to 10 g, was placed between crushed quartz, and in this way the reaction components had a uniform temperature when they came into contact with the catalyst. The reaction products were conveyed directly down into an alkaline water solution, which prevents any subsequent liquid phase reactions between unreacted starting products. The product mixture was analysed gas chromatographically, and in addition to the aromatic reacted and the nitro-aromatic formed, also the oxidation products benzyl alcohol, benzaldehyde and benzene were determined.

TABLE I

| Catalyst used | mmol nitro-aromatic formed per g of catalyst and hour |
| --- | --- |
| Crushed quartz | 0.023 |
| Mordenite | 0.25 |
| Montmorillonite | 1.03 |

In the above-mentioned table I, the results are shown of tests with different types of catalysts. The mordenite consists of a product from Norton, USA, with the designation Zeolon 200H, stated to have $SiO_2/Al_2O_3 = 10/1$. The montmorillonite was obtained from Süd-Chemie AG, Munich, and has the designation K 306 and the formula $Al_2O_3.4SiO_2.H_2O + XH_2O$. As will be noted from table I, crushed quartz gave practically no reaction whatsoever, while the Mordenite gave a substantial reaction, and the montmorillonite a still better reaction.

TABLE II

| Catalyst used | Partical size of catalyst, mm | mmol nitro-aromatic formed per g of catalyst and hour |
| --- | --- | --- |
| Montmorillonite | 2-3 | 1.03 |
| " | 0.2-0.5 | 5.73 |

In table II, the results of the most active catalyst (Montmorillonite) according to table I are compared when catalyst particles of different sizes are used. As will be noted, a reduction of the particle size from 2-3 mm to 0.2-0.5 mm gives a very substantial increase of the reaction.

TABLE III

| Catalyst used | mol relation aromatic/$HNO_3$ | mol relation nitro-aromatic/aromatic |
| --- | --- | --- |
| Montmorillonite | 3.5 | 4.5 |
| " | 1.4 | 39.0 |

Table III shows how the mol relation between nitro-aromatic formed and aromatic added is influenced by the mol relation between added aromatic and added $HNO_3$. An increase of the proportion of nitric acid gives a considerable increase of the quantity of nitro-aromatic formed.

TABLE IV

| Catalyst used | mmol aromatic per liter $N_2$ | nitro-aromatic in % of aromatic reacted |
| --- | --- | --- |
| Montmorillonite | 25.4 | 95 |
| " | 1.8 | 72 |

From table IV it will be noted that if the quantity of aromatic added per liter of nitrogen gas is reduced from 25.4 mmol to 1.8, the yield of nitro-aromatic will decrease, counted on the aromatic reacted from 95 to 72%. There is obviously no reason to reduce the quantity of aromatic added to less than approx. 25 mmol per liter of nitrogen.

TABLE V

| Catalyst used | nitrogen, liters per g of catalyst and hour | aromatic reacted in % of aromatic added |
|---|---|---|
| Montmorillonite | 0.7 | 8.2 |
| " | 2.0 | 54.3 |
| " | 5.0 | 4.7 |

In table V, finally, it is shown how the gas speed (measured in liters of nitrogen per g of catalyst and hour) influences the reaction of the aromatic added. The speed of 2.0 gives a considerably greater quantity of nitro-aromatic formed than the other two values.

In all of the tests accounted for above, toluene was used as an aromatic, but similar results have also been obtained with benzene.

The relation between the quantities formed of the different isomers of nitro-toluene has in all the tests using Montmorillonite as a catalyst been approx. 40:5:55 for ortho, meta, and para, respectively, which is considerably more favourable than at conventional nitration of toluene.

In all of the tests described above, the quantity of oxidation products formed, in the form of benzyl alcohol, benzaldehyde and benzene, have amounted to between 0.9 and 1.3% of the quantity of aromatic added, and has not shown any substantial change owing to the reaction conditions applied.

Most of the tests accounted for in the tables shown above have been carried out at 200° C. Minor deviations from this value which have occurred do not seem to have influenced the results.

We claim:

1. A method for preparing mononitrololuene through gas phase nitration of toluene, characterized in that gaseous toluene and nitric acid in a mol ratio of toluene/nitric acid of approximately 1.4, together with an inert carrier gas at a temperature of about 150° C. to about 250° C., are conveyed over a catalyst consisting essentially of an acidic silica-alumina zeolite-type catalyst, whereby the catalytic activity to produce mononitrolouene resides essentially in said zeolite-type catalyst.

2. A method for preparing mononitrotoluene through gas phase nitration of toluene, characterized in that gaseous toluene and nitric acid in a mol ratio of toluene/nitric acid of approximately 1.4, together with an inert carrier gas at a temperature of about 150° C. to about 250° C., are conveyed over a catalyst consisting essentially of montmorillonite, whereby the catalytic activity to produce mononitrotoluene resides essentially in said montmorillonite.

3. The method of claims 1 or 2 characterized in that said nitration is carried out at a temperature of about 170° C. to about 200° C., said carrier gas is nitrogen, said catalyst is finely divided and is in the form of 0.2-0.5 mm particles, the quantity of toluene added is about 25 mmol per liter of carrier gas; and the carrier gas speed is about 2 liters per gram of catalyst per hour.

4. The method of claim 3 characterized in that the nitration is carried out at a temperature of about 200° C.

5. A method for preparing monoitrotoluene through gas phase nitration of toluene, characterized in that gaseous toluene and nitric acid together with an inert carrier gas at a temperature of about 150° C. to about 250° C. and a carrier gas speed of approximately 2 liters per gram of catalyst per hour are conveyed over a catalyst consisting essentially of an acidic silica-alumina zeolite-type catalyst, whereby the catalytic activity to produce mononitrololuene resides essentially in said zeolite-type catalyst.

6. A method for preparing mononitrotoluene through gas phase nitration of toluene, characterized in that gaseous toluene and nitric acid together with an inert carrier gas at a temperature of about 150° C. to about 250° C. and a carrier gas speed of approximately 2 liters per gram of catalyst per hour are conveyed over a catalyst consisting essentially of montmorillonite, whereby the catalytic activity to produce mononitrotoluene resides essentially in said montmorillonite.

7. A method according to claims 5 or 6 characterized in that the mol ratio toluene/nitric acid is approximately 1.4.

8. A method according to claims 1, 2, 5 or 6 wherein said catalyst is in the form of 0.2 to 0.5 mm particles.

9. The method of claim 8 characterized in that said carrier gas is nitrogen.

10. A method according to claim 8 characterized in that the quantity of toluene added is approximately 25 mmol per liter of carrier gas.

11. A method according to claims 1, 2, 5 or 6 characterized in that the quantity of toluene added is approximately 25 mmol per liter of carrier gas.

12. The method of claims 1, 2, 5 or 6 characterized in that said carrier gas is nitrogen.

13. A method according to claim 12 characterized in that the quantity of toluene added is approximately 25 mmol per liter of carrier gas.

* * * * *